(12) United States Patent
Wagner et al.

(10) Patent No.: US 11,919,797 B2
(45) Date of Patent: Mar. 5, 2024

(54) METHOD AND APPARATUS FOR PRODUCING GLASS PRECURSORS AND GLASS PRODUCTS

(71) Applicant: SCHOTT AG, Mainz (DE)

(72) Inventors: Fabian Wagner, Mainz (DE); Michael Kluge, Offenbach (DE); Andreas Ortner, Gau-Algesheim (DE); Laura Brueckbauer, Ingelheim (DE); Frank-Thomas Lentes, Bingen (DE)

(73) Assignee: SCHOTT AG, Mainz (DE)

( * ) Notice: Subject to any disclaimer, the term of this patent is extended or adjusted under 35 U.S.C. 154(b) by 686 days.

(21) Appl. No.: 16/243,999

(22) Filed: Jan. 9, 2019

(65) Prior Publication Data

US 2019/0210909 A1     Jul. 11, 2019

(30) Foreign Application Priority Data

Jan. 10, 2018  (DE) .................... 10 2018 100 443.5

(51) Int. Cl.
   *A61J 1/06*   (2006.01)
   *A61M 5/31*   (2006.01)
   (Continued)

(52) U.S. Cl.
   CPC .......... *C03B 33/0955* (2013.01); *A61J 1/065* (2013.01); *A61M 5/3129* (2013.01); *B23K 26/53* (2015.10);
   (Continued)

(58) Field of Classification Search
   CPC .... A61J 1/05; A61J 1/06; A61J 1/065; A61M 5/178; A61M 5/31; A61M 5/3129; A61M 2205/12; A61M 2205/123; B32B 1/02; C03B 33/06; C03B 33/085; C03B 33/0855; C03B 33/095; C03B 33/0955; C03B 23/11–118; C03B 33/08; C03B 33/082;
   (Continued)

(56) References Cited

U.S. PATENT DOCUMENTS 4,254,883 A * 3/1981 Urban ..................... A61J 1/065
                                                         215/901
4,392,577 A * 7/1983 Maekawa ............. C03B 23/112
                                                         215/901
(Continued)

FOREIGN PATENT DOCUMENTS

CN          1564789        1/2005
CN          107428588      12/2017
(Continued)

*Primary Examiner* — Michael C Romanowski
(74) *Attorney, Agent, or Firm* — Ruggiero McAllister & McMahon LLC (57) ABSTRACT

A method and apparatus for producing glass products from tubular glass precursors is provided. In particular, a method and apparatus for separating tube glass into sized glass tube portions, produced glass tube portions, glass precursor portions, or glass product portions, and their use as pharmaceutical packaging are provided. The tube glass or the glass precursor or the glass product is provided with filaments along predetermined breaking planes. The filaments extend obliquely to the local wall radius and allow for clean separation of the tube glass or the glass precursor or the glass product.

16 Claims, 9 Drawing Sheets

(51) Int. Cl.
  *B23K 26/53* (2014.01)
  *C03B 33/02* (2006.01)
  *C03B 33/06* (2006.01)
  *C03B 33/095* (2006.01)
  *C03B 33/10* (2006.01)

(52) U.S. Cl.
  CPC .......... *C03B 33/0222* (2013.01); *C03B 33/06* (2013.01); *C03B 33/102* (2013.01); *A61M 2205/123* (2013.01)

(58) Field of Classification Search
  CPC .... B23K 26/359; B23K 26/36; B23K 26/362; B23K 26/364; B23K 26/50; B23K 26/53; B23K 15/08; B23K 15/085; B23K 15/10; B67B 7/92; B26K 2103/54
  USPC .............................................. 428/34.1–36.92
  See application file for complete search history.

(56) References Cited

U.S. PATENT DOCUMENTS

| | | | | |
|---|---|---|---|---|
| 5,779,753 | A * | 7/1998 | Vetter | C03C 23/0025 65/105 |
| 6,055,829 | A * | 5/2000 | Witzmann | C03B 33/0955 65/56 |
| 6,322,958 | B1 * | 11/2001 | Hayashi | B41M 5/24 219/121.85 |
| 6,438,996 | B1 * | 8/2002 | Cuvelier | C03B 33/0955 65/112 |
| 6,607,797 | B1 * | 8/2003 | Ritter | D03D 1/02 428/35.2 |
| 10,280,108 | B2 * | 5/2019 | Bohme | B23K 26/53 |
| 2001/0035447 | A1 * | 11/2001 | Gartner | C03B 33/09 225/2 |
| 2004/0231361 | A1 | 11/2004 | Moriya | |
| 2007/0158864 | A1 | 7/2007 | Van Stralen | |
| 2015/0034613 | A1 | 2/2015 | Hosseini | |
| 2015/0038313 | A1 * | 2/2015 | Hosseini | B23K 26/0648 219/121.75 |
| 2015/0136743 | A1 | 5/2015 | Hosseini | |
| 2015/0140241 | A1 * | 5/2015 | Hosseini | C03B 33/0222 65/102 |
| 2016/0009586 | A1 * | 1/2016 | Bookbinder | C03B 33/06 65/112 |
| 2016/0279895 | A1 * | 9/2016 | Marjanovic | B32B 17/06 |
| 2018/0022631 | A1 | 1/2018 | Förtsch | |
| 2018/0134606 | A1 | 5/2018 | Wagner | |
| 2018/0186679 | A1 * | 7/2018 | Wada | C03B 33/06 |
| 2018/0215648 | A1 * | 8/2018 | Wada | B23K 26/364 |
| 2018/0215649 | A1 * | 8/2018 | Wada | B28D 7/02 |
| 2019/0016623 | A1 * | 1/2019 | Lesche | C03B 33/095 |
| 2019/0099838 | A1 * | 4/2019 | Rieske | B23K 26/40 |
| 2019/0161383 | A1 * | 5/2019 | Deneka | C03B 29/025 |
| 2019/0193208 | A1 * | 6/2019 | Kalli | G02B 6/10 |

FOREIGN PATENT DOCUMENTS

| | | | | |
|---|---|---|---|---|
| DE | 3537434 | A1 * | 4/1987 | ................ A61J 1/06 |
| DE | 4214159 | C1 * | 11/1993 | ......... C03B 33/0955 |
| DE | 102015111490 | | 1/2017 | |
| DE | 102015111490 | A1 * | 1/2017 | ............. B23K 26/53 |
| EP | 2816017 | A1 * | 12/2014 | ............. A61J 1/065 |
| JP | 2001266739 | | 9/2001 | |
| WO | 2016007843 | | 1/2016 | |
| WO | 2017060252 | | 4/2017 | |
| WO | 2017073118 | | 5/2017 | |

* cited by examiner

METHOD AND APPARATUS FOR PRODUCING GLASS PRECURSORS AND GLASS PRODUCTS

CROSS REFERENCE TO RELATED APPLICATIONS

This application claims benefit under 35 USC § 119 of German Application 10 2018 100 443.5 filed Jan. 10, 2018, the entire contents of which are incorporated herein by reference.

BACKGROUND

1. Field of the Invention

The invention relates to a method for producing glass precursors and glass products, to an apparatus for producing glass precursors or glass products, to a tubular glass precursor or glass product, to glass tube portions or glass precursor portions or glass product portions, and to their use for pharmaceutical packaging.

More particularly, the invention relates to a method for separating tube glass into sized glass tube portions, to an apparatus for preparing the separation of tube glass into sized glass tube portions, and to glass tube portions produced by such method and their use. The terms tube glass or glass precursor shall be understood to include also partially non-circular elongated hollow bodies and elongated hollow bodies with varying diameter along the longitudinal extension thereof.

2. Description of Related Art

For separating glass tube portions from tube glass, it has been known to mechanically scribe and then break the tube glass. The breaking can also be achieved through thermal shock, by obtaining a warm glass tube by continuous belt-drawing from the melt, contacting it with a cool tool and thereby introducing a defect into a small area of the lateral surface of the tube, which defines the fracture plane.

A drawback of these prior art methods is the inaccuracy of the length of the separated glass tube portions and insufficient quality of the fracture surfaces at the tube ends. Splinters are caused when breaking the tubes, and the tube ends have a reduced strength. Therefore, the tube ends typically undergo post-processing, and splinters or particles resulting from the breaking are removed by washing processes. This makes the fabrication of tubular glass precursors, such as those required for producing glass products for the pharmaceutical industry, more expensive.

From US 2015/0034613 A1 it is known to produce continuous laser filaments in transparent materials. A burst of ultra-fast laser pulses is focused on the transparent material which is in the form of sheets.

US 2015/0140241 A1 discloses the producing of a spiral cut transparent tube, wherein a continuous laser filament is formed through the transparent tube. Individual rings can be separated from the tube end, or a helical glass spiral is separated. The method is very energy consuming.

WO 2016/007843 A1 relates to the cutting of glass articles by inducing pulsed laser perforations in the glass. Inter alia, a cylindrical tube is disclosed rotating relative to a pulsed laser assembly, and radial laser perforations are cut into the tube around the circumference of the glass tube, such perforations presenting themselves as defects, recesses, or holes in the glass. Such accurate tight holes facilitate the subsequent separation around the perforation line. It is also possible to rotate a rotatable arm of the pulsed laser assembly around the glass article thereby cutting the orbited tube.

WO 2017/060252 A1 relates to a method for producing a workpiece from a dielectric material, which workpiece has at least one zone with a strength set in a defined manner, and the zone of defined strength has cavities. WO 2017/060252 A1 furthermore relates to a workpiece produced by this method. The cavities in the workpiece are produced using a pulsed laser with radiation that is shaped according to a paraxial focus of a lens. Passage-like cavities are generated, which perforate the workpiece partially or completely and which are oriented orthogonally to the surface of the workpiece.

SUMMARY

An object of the invention is to provide a method and an apparatus for producing glass products from tubular glass precursors and to provide tubular glass precursors or glass products.

Furthermore, the present invention is based on the object to separate tube glass or glass precursors by breaking it into sized portions without producing splinters or particles at the fracture surface. This aims to avoid washing processes and possible post-processing of the tube ends without however accepting a high-energy laser-based separation method.

Tube glass that can be used includes pharmaceutical tubing of up to 50 mm in diameter, or technical tube, e.g. made of Duran® glass.

Glass precursor refers to reshaped tube glass, for example divided into tube glass portions, inter alia.

Glass products that are to be produced include ampoules, cartridges, and syringe bodies. It shall be possible to provide such products with predetermined breaking points for later separation.

According to the invention, a tube glass or tubular glass precursor is provided with filaments along predetermined breaking planes, wherein the filaments extend obliquely to the local radius, which makes it possible to properly separate the tube glass or glass precursor, or a glass end product. For the purposes of the invention, filament refers to linear or filament-shaped defects in the glass extending from outside into the interior of the glass body.

The method for producing glass precursors and glass products comprises the following steps: providing stationary or moved glass tube in terms of translational movement; laser-based irradiation of the glass tube with focused radiation to produce filaments in a desired separation plane of the glass tube; wherein the irradiation with focused radiation in the separation plane for producing the filaments is executed at an oblique irradiation angle (a) deviating from the perpendicular to the local surface of the glass tube; separating the sized glass tube portion by mechanically or thermally induced (tensile) stress in the separation plane of the glass tube and creating a fracture surface along the separation plane.

In particular, the method according to the invention for separating tube glass into sized glass tube portions works with the following steps: providing glass tube; laser-based irradiation of the glass tube with focused radiation at an oblique irradiation angle to produce filaments in a desired separation plane of the glass tube, wherein the irradiation with focused radiation in the separation plane for producing the filaments is executed at an oblique irradiation angle deviating from the perpendicular to the local surface of the glass tube; and separating the sized glass tube portion by mechanically or thermally induced stress in the separation plane of the glass tube and creating a fracture surface along the separation plane.

In the providing step, the glass tube or tubular glass precursor can be provided in stationary or moved manner in terms of translational movement in the direction of the longitudinal axis. When provided stationary in terms of translation, the glass tube or the tubular glass precursor may be rotated about its longitudinal axis during processing. This is followed by an intermittent translational movement of the glass tube or glass precursor.

A peculiarity of the method according to the invention is that in the laser irradiation step, the irradiation in the separation plane for producing the filaments is effected in an oblique irradiation angle deviating, by a few degrees, from the vertical to the local surface. The oblique irradiation angle in the separation plane may be in a range from less than 90° to 70°, preferably in the range from 89.5° to 75°, more preferably in the range from 89° to 80°, and most preferably in the range between 85° and 80°, relative to the tangent to the glass tube or to the tubular glass precursor at the point of incidence of the laser beam.

It has been found that if, in contrast to the invention, the irradiation is executed orthogonally to the tangent of the tube surface or glass precursor surface in order to define the fracture plane of the tube glass or glass precursor by filaments, splinters or particles larger than 100 μm are caused at the inner surface of the glass tube or glass precursor upon separation of glass tube portions or glass precursor portions, which would require washing processes and possibly further finishing processing of the glass tube or glass precursor because of an increased roughness in the fracture surface. Surprisingly, it has been found that the causing of splinters and particles can be avoided if the filaments in the desired separation plane are formed according to the invention, namely at an oblique angle to the local surface of the glass tube or glass precursor, and that a smoother fracture surface is achieved in this way than in the case of filaments orthogonal to the surface of the glass tube or glass precursor. The respective best magnitude of the oblique irradiation angle is determined experimentally as a function of wall thickness and local diameter of the glass tube or glass precursor. As a rule, the smaller the diameter, the greater is the oblique irradiation angle. Thus, the effect of avoiding splinters and particles when separating the glass tube portions or glass precursor portions can be maximized by an appropriate combination of oblique irradiation angle and local diameter.

In practice, the oblique irradiation angle is achieved by working with an offset of the focused radiation with respect to the radial direction, measured on the surface of the glass tube or glass precursor. In other words, the irradiation direction is offset laterally to the axis of the glass tube or glass precursor. For glass tubes or glass precursors having a local diameter ranging from 3 mm to 50 mm, preferably ranging from 5 to 40 mm, the offset is in a range from 0.1 mm to 3 mm, preferably in a range from 0.5 mm to 2 mm. It will be understood that with the offset, the focus position of the focusing optics has to be readjusted as well.

When fabricating glass products from tubular glass tube products, a desired separation plane can be produced as a predetermined breaking plane, for example glass products in the form of ampoules.

The invention also relates to an apparatus for producing tubular glass precursors or glass products. Such an apparatus may relate to the separation of tube glass or glass precursors into sized portions along a desired separation plane. The apparatus comprises a feeding device for tube glass or glass precursor, a laser-based irradiation device for generating focused radiation along a desired separation plane in an oblique irradiation angle relative to the local surface of the glass tube or glass precursor by means of focusing optics, a guiding device for stably guiding and supporting the focusing optics along a desired separation plane at a desired distance and in the desired oblique irradiation angle relative to the surface of the glass tube or glass precursor, and a take-off device. With the apparatus according to the invention, the irradiation in the separation plane for producing the filaments is effected in an oblique irradiation angle deviating from the perpendicular to the local surface of the glass tube or glass precursor. The separation of the sized glass tube portion is achieved in separation devices that are known per se, which cleave the glass tube or the glass precursor by mechanically or thermally induced stress so as to create a clean fracture surface in the separation plane of the glass tube or glass precursor thereby obtaining perfect portion end faces.

The feeding device for glass tube or glass precursor is adapted to intermittently or continuously advance, i.e. translate, the glass tube or the glass precursor in the direction of the longitudinal axis. At the same time, the glass tube or glass precursor may be rotated when the laser-based irradiation device generates stationary focused radiation. When the tube is held stationary, focused radiation is generated so as to rotate around the glass tube or glass precursor.

The feeding device may be part of a glass tube producing apparatus or of a glass tube shaping apparatus feeding the glass tube or glass precursor to the laser-based irradiation device, optionally still in the hot state. Suitable shaping processes for the glass tube or the glass precursor include fabrication processes according to Danner, Vello, or else an overflow fusion process. In the Danner process, a stream or strand of molten glass runs onto an obliquely inclined rotating spindle. By the rotating, the glass is distributed about the circumference of the spindle while flowing along the spindle toward the lower end thereof. In the Vello process, the molten glass exits through an annular nozzle. The diameter of the resulting tube can be increased and adjusted by introducing compressed air.

If the method is to be executed on a moving glass tube or glass precursor, for example if the method is to be carried out on a continuously formed tubular glass body directly as drawn from the melt or after partially melting a glass body, then it is preferred for the laser-based irradiation device to be configured so as to move concomitantly along the feeding direction of the glass tube or glass precursor. In this way it is possible to perform the focused irradiation around the glass tube or glass precursor in the desired separation plane in order to prepare the glass tube or glass precursor for being separated. Depending on the work program, the separation is executed immediately after the preparation of separation or at a later time. The work may also be effected in mixed manner, for example by performing an immediate separation which is followed by a separation to be carried out later, so that tubular bodies are separated which include a portion with prepared predetermined breaking point. Such tubular bodies are intermediate products in the fabrication of, for example, ampoules that are provided with a predetermined breaking point. According to one embodiment of the invention, a portion of a glass tube or glass precursor is accordingly provided, which includes, between the end face fracture surfaces, at least one predetermined breaking plane with filaments extending obliquely relative to the local radius. The predetermined breaking plane lies preferably perpendicular to the longitudinal axis of the tubular portion, but it is also conceivable to introduce this plane obliquely to the longitudinal axis, so that the longitudinal axis cuts the plane at an oblique angle.

The laser-based irradiation device may comprise a laser, focusing optics, and a light guide connecting them. For example hollow glass fibers are suitable as a light guide for the intense laser pulses. The guiding device may form part of a robot that is capable of stably guiding the focusing optics around the glass tube or glass precursor at the desired distance and in the desired angular orientation relative to the surface of the glass tube or glass precursor in a desired separation plane of the glass tube or glass precursor. Depending on whether the glass tube or glass precursor is stationary or moved during the processing, the robot arm can be guided around the glass tube or glass precursor stationarily or in concomitantly moving manner. In both embodiments, the focusing optics may be accommodated in a guide head that includes a sensor for determining the distance to the surface of the glass tube or glass precursor and the position of the produced filaments.

In a further embodiment, the laser-based irradiation device comprises a rotatable scanner head with beam guidance to the focusing optics that is arranged on the inner surface of an annular mirror that defines an annular space through which the tubular body to be processed extends. If moving glass tube or glass precursor is to be processed in this embodiment, the laser-based irradiation device has to be adapted so as to move concomitantly with the moving glass tube or glass precursor. If this shall be avoided and a stationary irradiation device shall be provided, an annular mirror is used which comprises portions arranged along a helical spiral. The movement of the glass tube or glass precursor is synchronized to the scanning revolution of the irradiation device such that the filaments are produced in the desired separation plane of the glass tube or glass precursor.

Instead of lenses it is possible to use portions of the annular mirror, which are designed as imaging optics. The combination of curved mirrors and lenses as imaging optics is possible as well.

It is also possible to arrange a plurality of rotatable scanner heads around the glass tube or glass precursor to be processed.

The invention also relates to glass tube portions or glass precursor portions produced according to the method of the invention. Such portions have a fracture surface at the ends of the portion featuring broken open filaments that extend obliquely to the respective local radii of the tube. The glass tube portion or glass precursor portion according to the invention may constitute an intermediate product, for example on the way to a final product such as an ampoule. Since the intermediate product has a clean fracture surface free of any chipping or particles greater than 150 µm, preferably greater than 100 µm, more preferably greater than 50 µm, most preferably greater than 20 µm, the further processing into a final product is more cost effective and also safer, compared to prior art glass tube portions. The glass tube portions or glass precursor portions preferably have a hollow cylindrical shape with annular end faces that are defined by the fracture surfaces. However, the glass tube portion or glass precursor portion may also have an elliptical or, more generally, non-circular cross sectional shape.

Glass precursors according to the invention with integrated predetermined breaking point may also constitute end products, such as an ampoule that has a prepared fracture surface which is to be opened by the user of the ampoule. Here, too, it is desirable that the fracture surface does not feature any chipping or particles larger than 50 µm or 100 µm.

In the glass tube portion or glass precursor portion according to the invention, the filaments should be spaced apart from each other by 2 to 15 µm, preferably by 3 to 12 µm, more preferably by 4 to 8 µm, measured on the outer surface or lateral surface of the glass tube or glass precursor. The filaments may belong to two or more filament areas which are distributed around the circumference of the glass tube or glass precursor and separated by unaffected areas. Each filament area comprises a set of individual filaments which themselves are spaced apart from each other. In this way, cost and effort for producing the prepared fracture points is significantly reduced.

The unaffected areas between the filament areas may have an extent of at least 50 µm or at least 100 µm, measured in the circumferential direction of the glass tube or glass precursor. The number of filament areas distributed around the circumference of the glass tube or glass precursor may amount to up to twelve areas. The filament areas should occupy at least 8%, preferably at least 16%, and most preferably at least 32% of the circumference of the glass tube or glass precursor.

The invention also relates to the use of glass products produced according to the invention for pharmaceutical packaging, such as ampoules.

BRIEF DESCRIPTION OF THE DRAWINGS

Exemplary embodiments of the invention will now be described with reference to the drawings, wherein.

DETAILED DESCRIPTION

Figure 1:
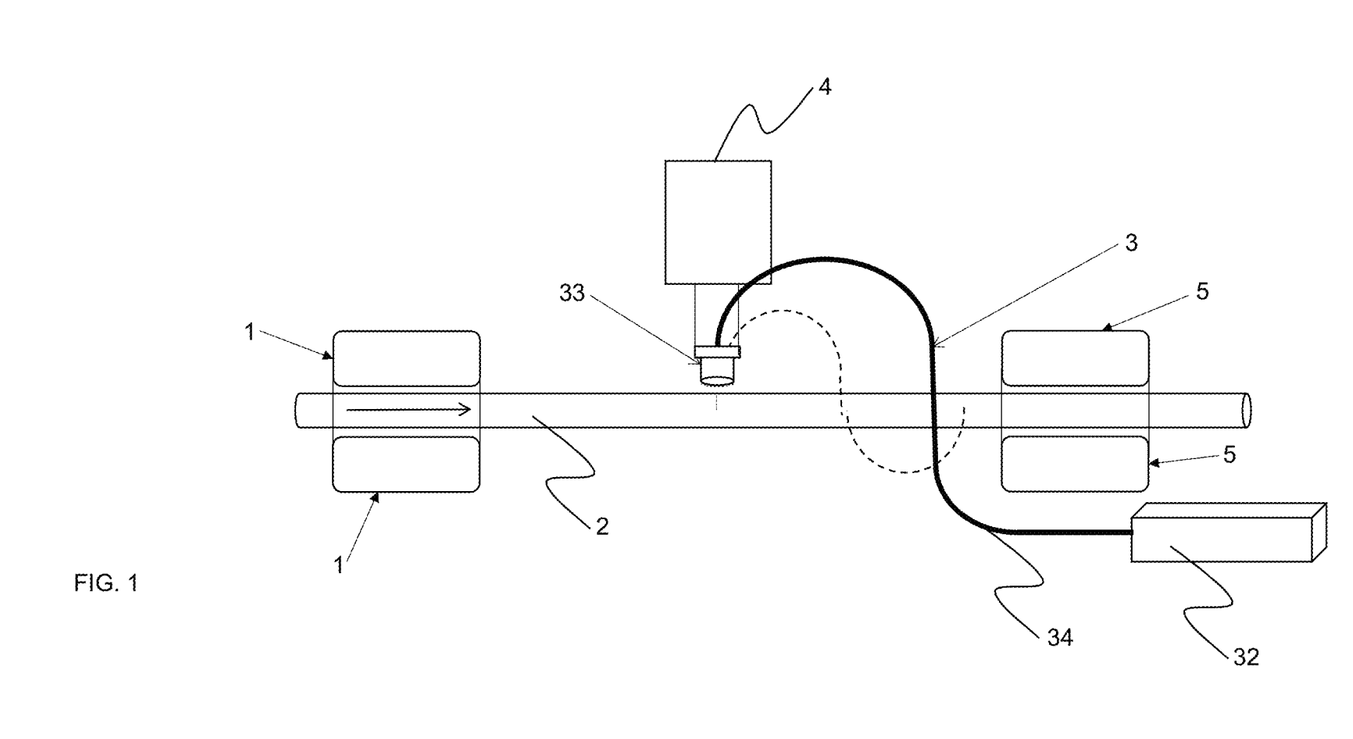
FIG. 1 is a first schematic view of an irradiation device for producing filaments in a glass tube.
Figure 10:
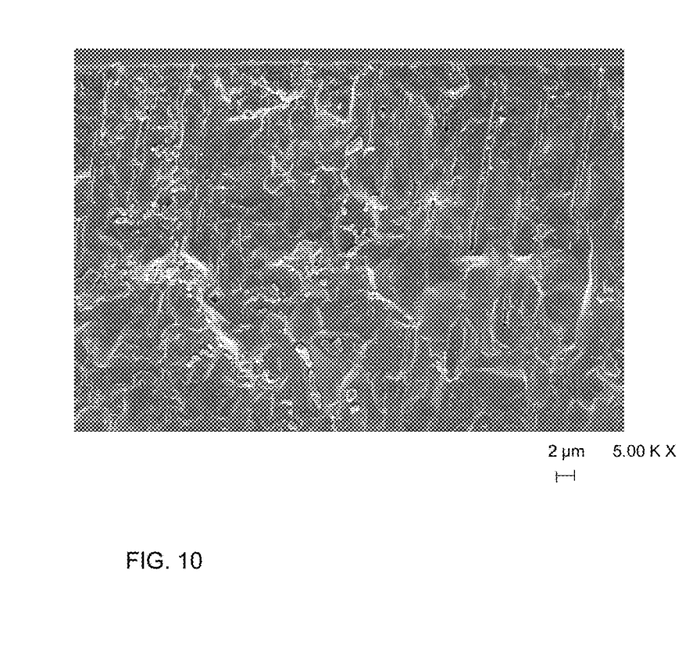
FIG. 10 shows an enlarged section of FIG. 9.
Figure 11:
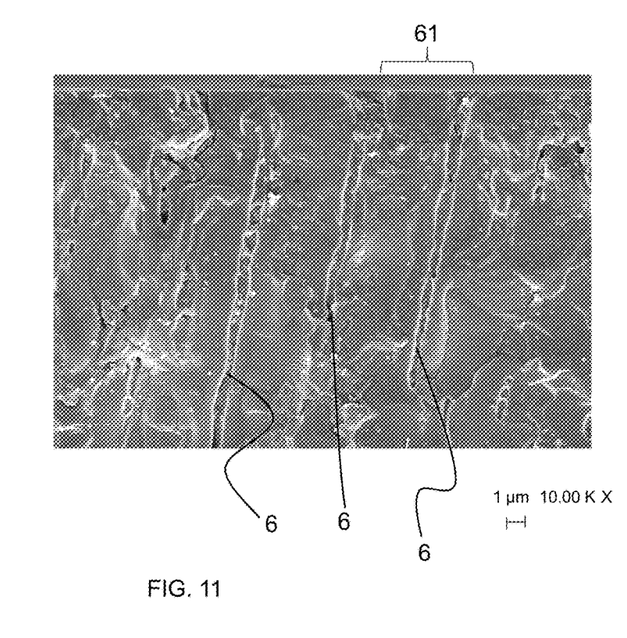
FIG. 11 shows a further enlarged section of FIG. 10.

FIG. 1 shows an apparatus for preparing the separation of tube glass into sized glass tube portions. The apparatus comprises a feeding device 1 for glass tube 2, a laser-based irradiation device 3 for generating focused radiation 30 (FIG. 8) by means of focusing optics 31 (FIG. 7), a guiding device 4 for stably guiding and supporting the focusing optics at the desired distance and in a desired oblique irradiation angle α (FIG. 6) relative to the surface of the glass tube 2, and a glass tube take-off device 5. Laser-based irradiation device 3 comprises a laser 32, a guide head 33 for the focusing optics 31, and a hollow fiber 34 connecting the laser 32 to the focusing optics 31. The guide head 33 furthermore includes sensors 35, 36 (FIG. 7) for determining the distance of focusing optics 31 to the surface of the glass tube 2 and the position of produced filaments 6 (FIGS. 10 and 11). The guide head 33 is guided by the guiding device 4, which may form part of a robot, such that the focusing optics 31 within the guide head 33 can be guided around the glass tube at the desired distance and in the desired angular orientation with respect to the surface of the glass tube 2 and in a desired separation plane of the glass tube.

A suitable laser for an apparatus according to the invention is a neodymium-doped yttrium-aluminum-garnet laser with a wavelength of 1064 nanometers, which may also be operated in a frequency-doubled mode. In this case, a suitable pulse duration of a laser pulse is preferably shorter than 100 picoseconds, more preferably shorter than 10 picoseconds.

Figure 6:
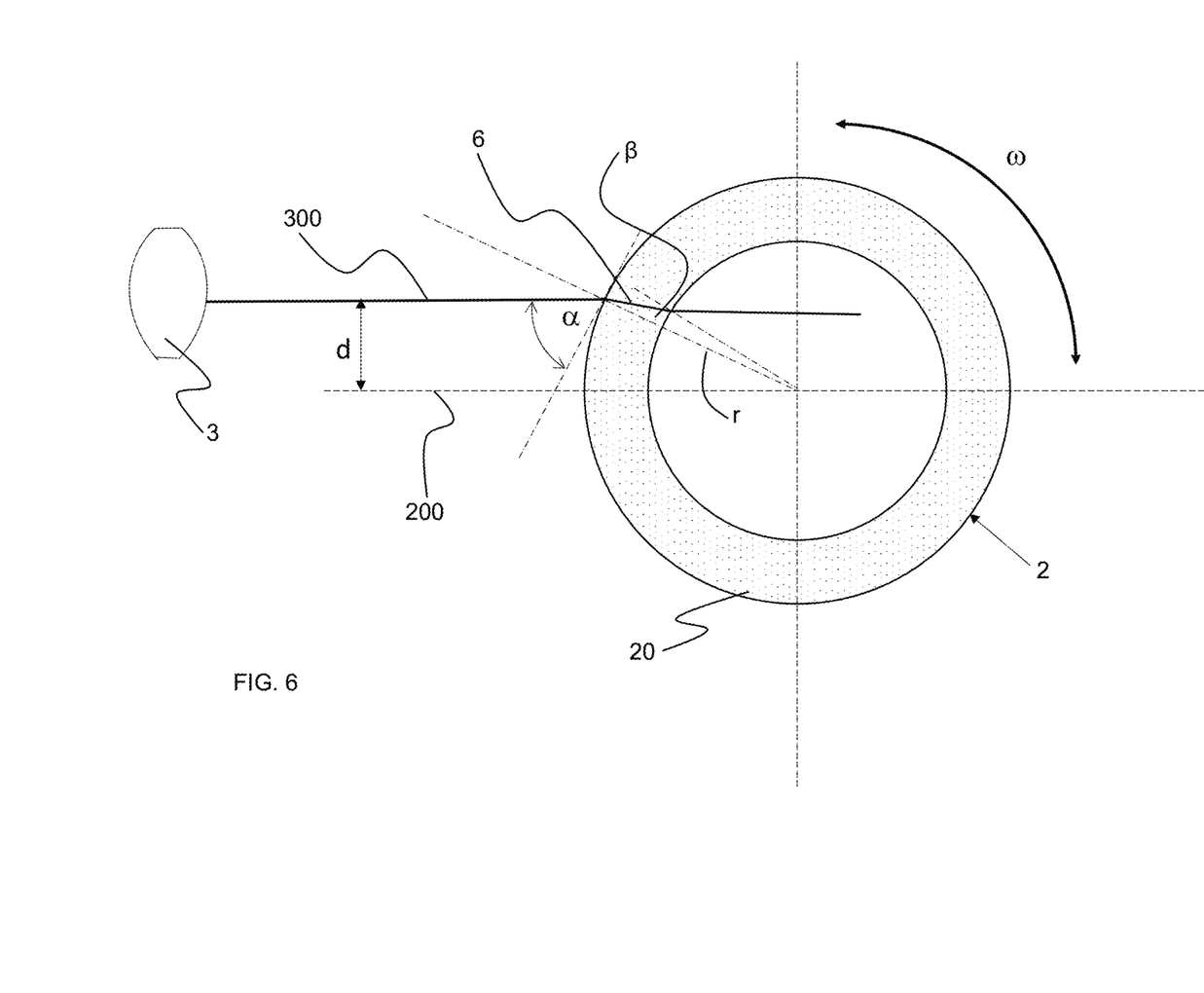
FIG. 6 is a geometric diagram illustrating the orientation of the irradiation device relative to the glass tube to be processed.

FIG. 6 shows the scheme for producing filaments 6 in the separation plane 20 of glass tube 2. Indicated therein is the radius vector 200 which is perpendicular to the surface of glass tube 2, and the irradiation axis 300 of focused radiation 30, which are offset in parallel to each other by an offset d. Thus, the oblique irradiation angle $\alpha$ is resulting. Due to refraction in glass, the irradiation axis is refracted towards the axis of the tube, resulting in an angle $\beta$ between the local radius vector r and the local axis of irradiation. Furthermore, it is intended that the glass tube 2 and the irradiation device 3 are rotated relative to each other in increments of an angular velocity $\omega$.

Figure 7:
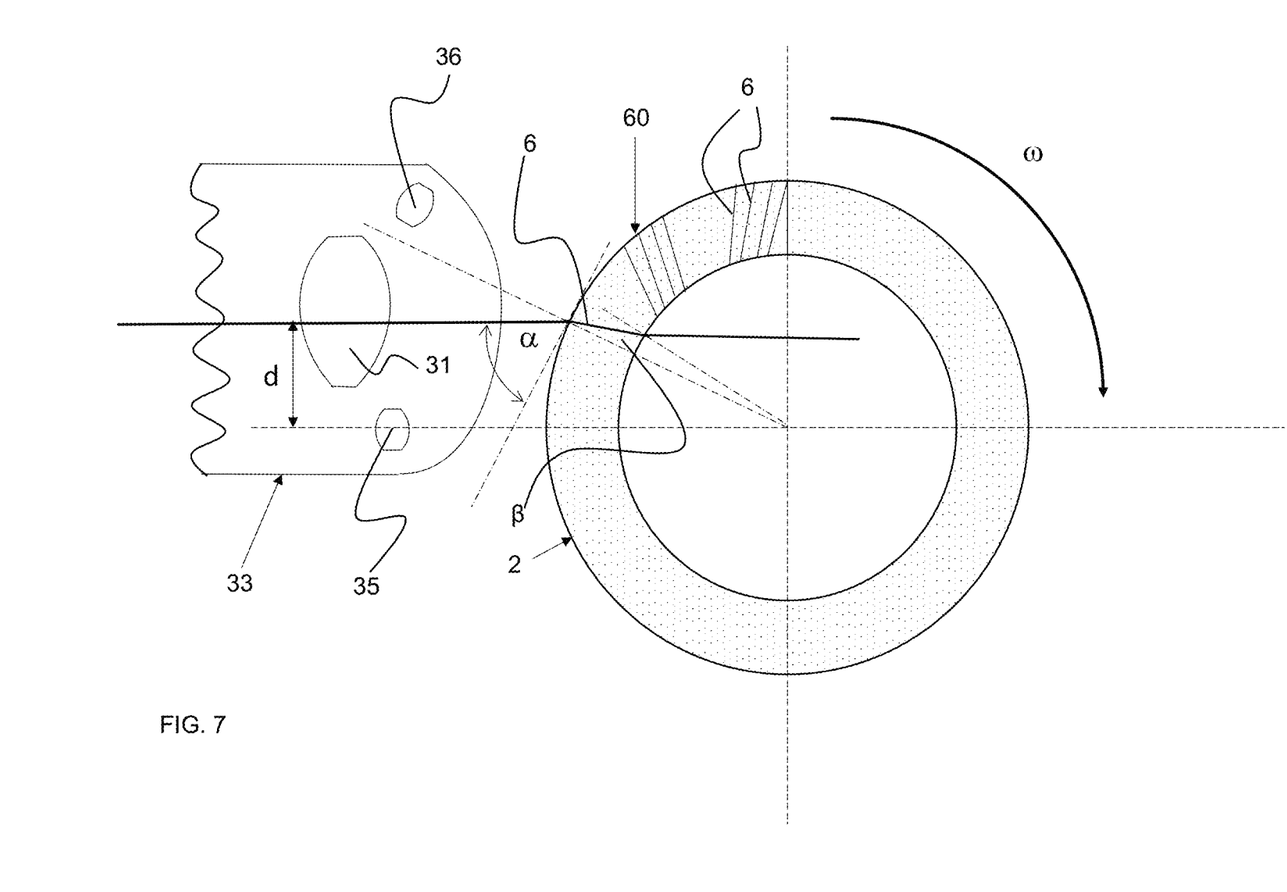
FIG. 7 is a schematic view of a guide head with integrated irradiation device.

FIG. 7 shows an enlarged section of FIG. 6, although with sets 60 of filaments 6, which have been produced after corresponding incremental rotations of the glass tube 2 (with altered position of the guide head 33). Furthermore, the guide head 33 is illustrated schematically, including the focusing optics 31 and sensors 35, 36, wherein sensor 35 is used as a distance sensor for determining the distance of focusing optics 31 from glass tube 2 and sensor 36 is used as a scanning sensor for identifying produced filaments 6.

Figure 8:
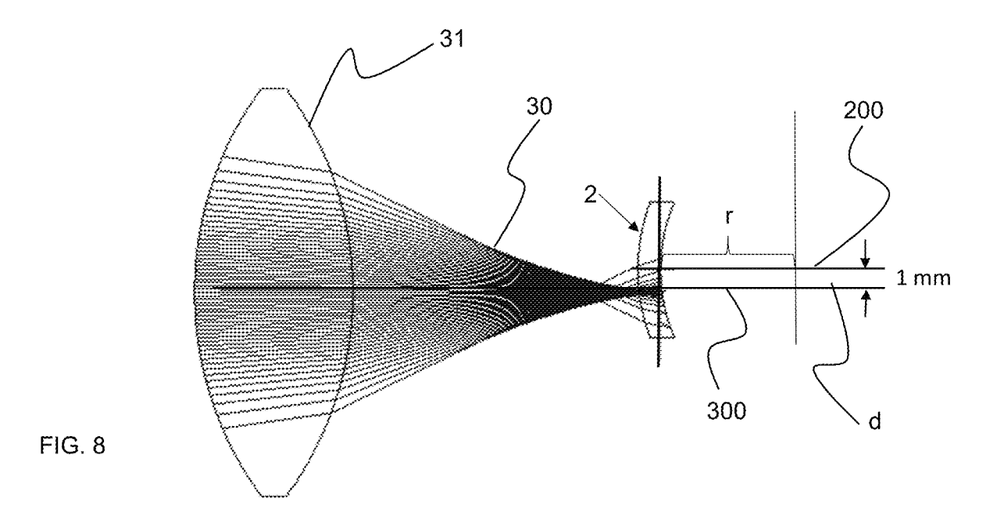
FIG. 8 illustrates irradiation optics at a decentered position with respect to the local surface of a glass tube.

FIG. 8 shows an enlarged computer-generated scheme of focused radiation 30 for producing filaments 6 in a glass tube 2 that has an inner radius r. The offset d between radius vector 200 and irradiation axis 300 is approximately 1 mm for a glass tube having an inner radius of r=6 mm.

Figure 9:
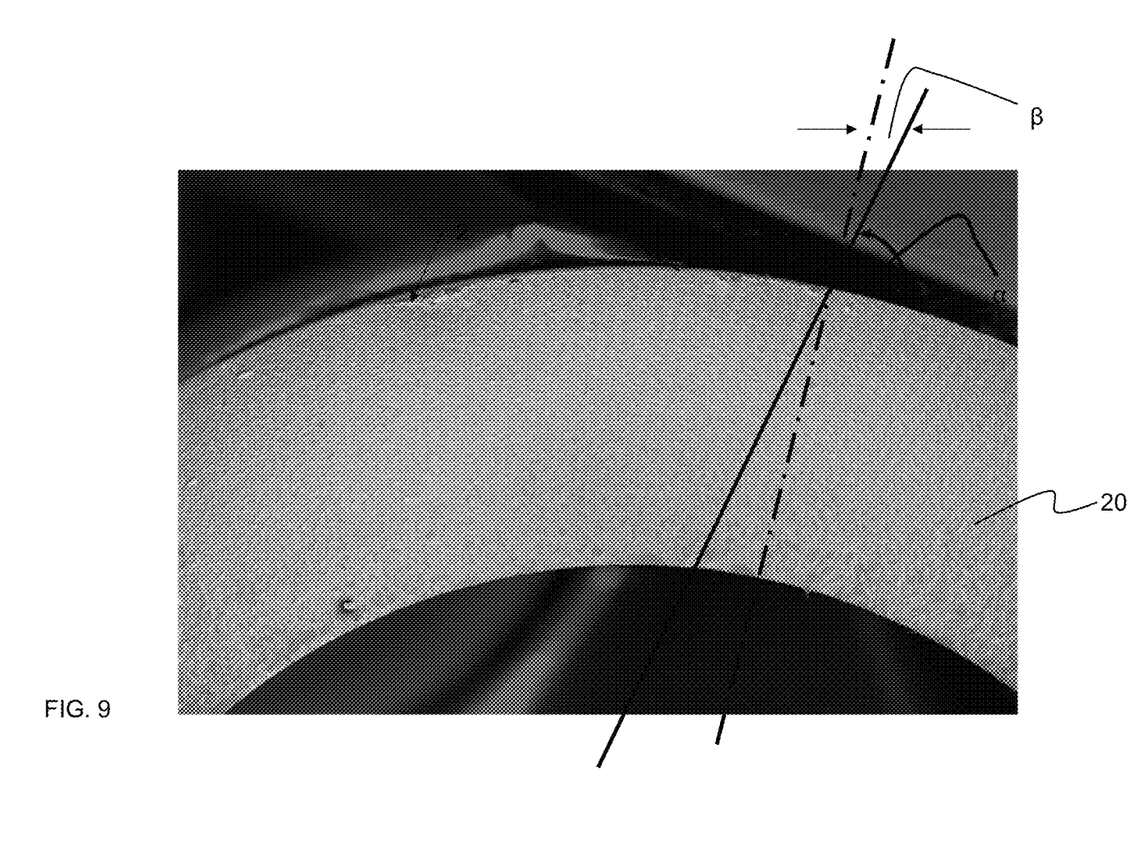
FIG. 9 shows an enlarged portion of a fracture surface of a glass tube with obliquely extending filaments.

FIG. 9 shows an enlarged micrograph of the separation plane 20 as a fracture surface featuring a multitude of filaments 6 that extend obliquely to the local radius vector, at an angle $\beta$.

FIGS. 10 and 11 show further enlarged micrographs of the separation plane 20 as a fracture surface featuring opened filaments 6 which extend at a spacing 61 from each other.

Such filaments 6 have been produced using a laser-based irradiation device 3 comprising a biconvex lens with a focal length of 16 mm and an aperture of 18 mm. The laser emitted radiation of a wavelength of 1064 nm, with pulse energy>200 µJ, burst energy of 100 µJ for 4 bursts, and with a burst frequency of 50 MHz. Pitch was 8 µm, focal position was −1.25 mm, and offset was d=1 mm. The glass tube had an outer diameter of 6.85 mm and a wall thickness of about 1 mm.

The feeding device 1 may be a device for drawing glass from the melt, or else a redrawing device. However, it is also possible to use a discontinuously operated feeding device. Depending on whether the glass tube 2 is stationary or in longitudinal advancement when introducing the filaments 6, the guide head 33 will perform a rotational movement or a helical movement in space, but always in alignment with the surface of the glass tube 2. The rotational movement or helical movement of the guide head 33 can be considered as an orbital revolution of the irradiation device 3 with respect to the desired separation plane 20. The orbital movement is synchronized with the movement of the glass tube 2 such that the radiation 30 emitted by the irradiation device and guided by the guide head 33 always propagates in the desired separation plane 20. Here, the focused radiation 30 is not incident centrically on the glass tube 2, but at a specific offset d to the radius (FIG. 6), so that an oblique irradiation angle $\alpha$ is resulting relative to the local tangent to the glass tube, which may range from less than 90° to 70°, preferably from 89.5° to 75°, more preferably from 89° to 80°, most preferably between 85° and 80°. The optimum oblique irradiation angle $\alpha$ depends on the tube's diameter and on the optical properties of the material. The respective most favorable value is determined by tests or calculations.

Figure 2:
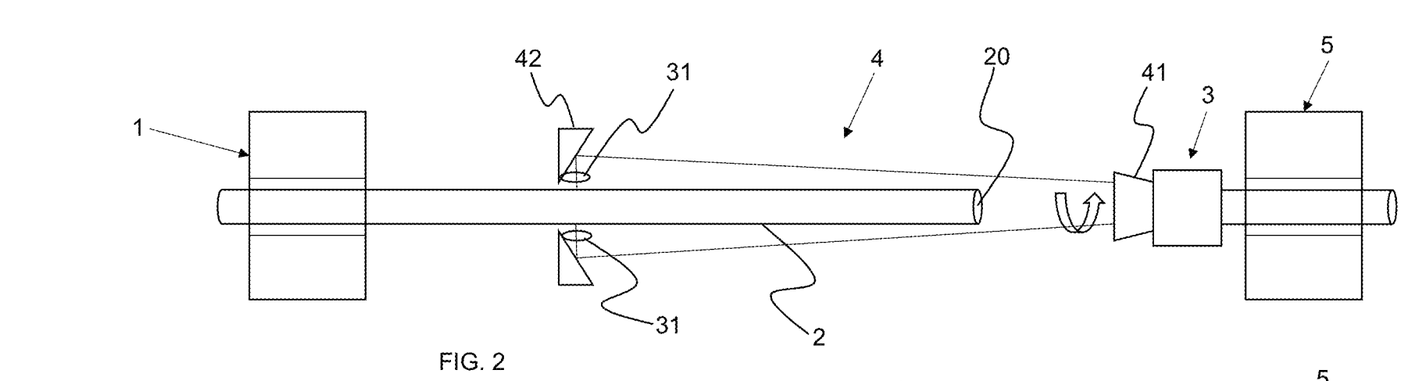
FIG. 2 is a second schematic view of an irradiation device comprising a rotatable scanner head.

FIG. 2 shows an embodiment of the apparatus for preparing the separation of tube glass into severed glass tube portions 21 (FIG. 5), in which the laser-based irradiation device 3 comprises a rotatable scanner head 41 with beam guidance to the focusing optics 31 disposed on the inner surface of an annular mirror 42 that defines an annular space through which the glass tube 2 to be processed extends. The rotatable scanner head 41 and the annular mirror 42 together form a guiding device 4 for focusing optics 31. The irradiation device 3 comprises one or more lasers (not shown) for simultaneously supplying one or more laser beams to the focusing optics 31. The annular mirror 42 has a faceted inner surface which is inclined towards the glass tube 2 which extends through the annular space of annular mirror 42. The facets ensure that an oblique irradiation angle $\alpha$ is maintained.

The embodiment of the apparatus according to FIG. 2 is designed for stationary operation. The glass tube 2 is intermittently advanced and locked, whereupon the filaments 6 are produced in a desired separation plane 20 of the glass tube 2 by operation of the irradiation device 3. The filaments 6 extend obliquely, as shown in FIGS. 9 to 11.

The embodiment of FIG. 2 can also be built for continuous operation. The distance between feeding device 1 and glass tube take-off device 5 is increased to at least twice the distance shown in FIG. 2. Furthermore, the laser-based irradiation devices 3 and the guiding device 4 are configured for moving concomitantly with the glass tube 2 feeding device 1. In this way, the filaments 6 can be produced in the desired separation plane during the concomitant movement. Thereafter, the guiding device is returned to its initial position, to immediately again move forward together with the advancing glass tube.

Figure 3:
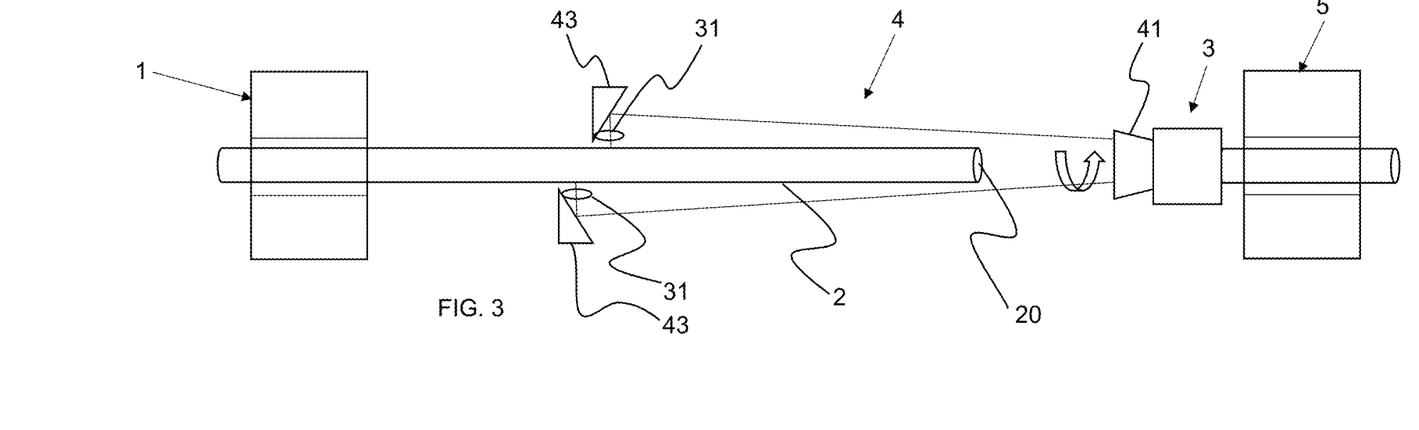
FIG. 3 is a third schematic view of an irradiation device with a helical mirror.

The embodiment of the apparatus according to FIG. 3 represents a modification of the embodiment of FIG. 2. The mirror comprises mirror portions 43 arranged along a helix. Glass tube 2 can be advanced continuously while being provided with the filaments 6 in the desired separation plane. The mirror portions 43 are successively exposed to the laser beam in synchronization with the advancement rate of the glass tube such that the filaments 6 are produced in the desired separation plane.

Figure 4:
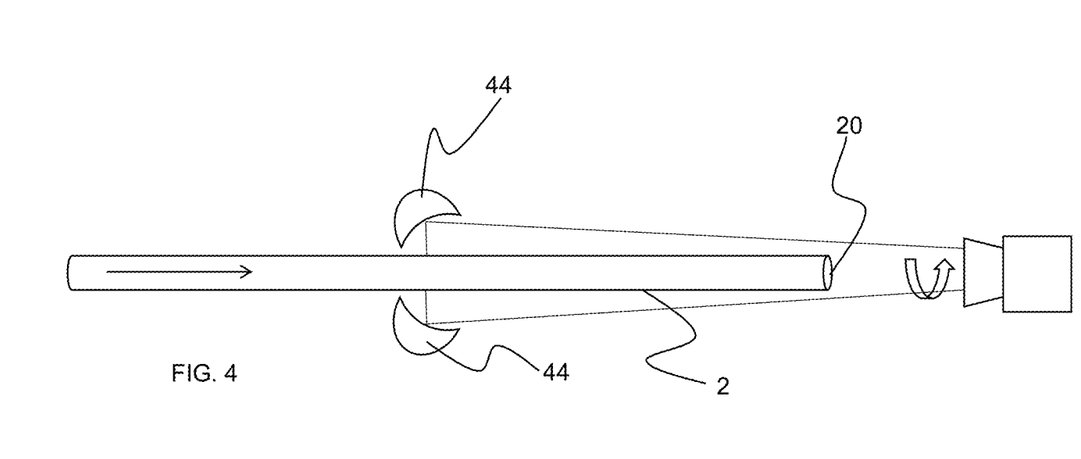
FIG. 4 is a fourth schematic view of an irradiation device with imaging optics annular mirror.

FIG. 4 shows an embodiment of the apparatus in which the annular mirror comprises portions 44 that are designed as imaging optics. The imaging optics are suitable for tube glass with radii greater than 10 mm. If the radii are smaller than 10 mm, intermediate optics (not shown) similar to the focusing optics 31 of FIGS. 2 and 3 are used additionally, so that the injection angle of the laser irradiation can be enlarged and the filament 6 in the interior of the glass tube 2 will be more pronounced than without this measure.

Intermediate optics between the focusing optics 31 and the glass tube surface may also be used in the embodiments of FIGS. 1 to 3. It is also possible to use an immersion liquid with a high refractive index compared to air as intermediate optics, where this is feasible.

Figure 5:
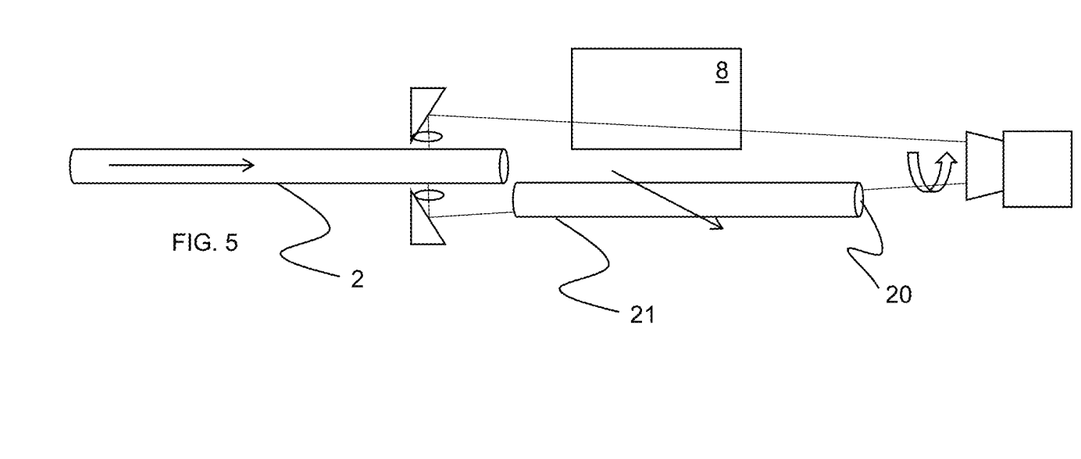
FIG. 5 shows an irradiation device with glass tube portion separation device.

FIG. 5, in which the feeding device and the take-off device for glass tube 2 has been omitted, shows a further embodiment. The configuration corresponds to the embodiment of FIG. 2. The glass tube 2 is advanced intermittently, and the separation plane is marked with filaments 6. However, separation of the sized glass tube portion is achieved still within the apparatus. For this purpose, a separation device 8 is employed, which subjects the glass tube 2 to a mechanical pressure or to a cold shock at the separation point, so that a glass tube portion 21 is separated from the supplied glass tube 2. The separated glass tube portion 21 is removed by some means (not shown).

The fracture surface generated along separation plane 20 exhibits a certain roughness, as can be seen in the micrographs of FIGS. 9 to 11. However, the fracture surface is free of particles, if 'particle' is understood to mean chippings greater than 150 µm or 100 µm, or 50 µm, or even only 20 µm. Striking traces that can be seen in the fracture surface are obliquely extending broken open filaments 6. The filaments 6 are laser-generated channel-like perforations or partial perforations in the tube wall of glass tube 2. The inclination angle β (FIG. 6) defined between the extension of filaments 6 and the local tube radius r is in a range from 1° to 15°, with tubes of larger diameter exhibiting the smaller angles and tubes of smaller diameter exhibiting the larger angles. Angle values in the range from 5° to 10° have proved to be most advantageous. Filaments 6 have a filament spacing 61 from each other ranging from 2 µm to 15 µm. A range of spacings between 4 µm and 8 µm is preferred.

The fracture surface need not be continuously covered by filaments 6, as is illustrated in FIG. 7. Filament areas 60 may alternate with unaffected areas. The filament areas 60 each comprise a set of individual filaments 6, which are themselves spaced apart, as mentioned previously. The unaffected areas between the filament areas 60 may have an extent of at least 50 µm or at least 100 µm, measured in the circumferential direction of the tube. The number of filament areas 60 (and therefore also that of unaffected areas) is up to twelve areas, which are distributed around the circumference of the glass tube. The filament areas 60 occupy at least 8%, preferably at least 16%, or most preferably 32% or more of the circumference of the glass tube. Thus, the separation of tube glass into glass tube portions can be achieved with little energy consumption, and yet clean fracture surfaces can be achieved.

Figure 12:
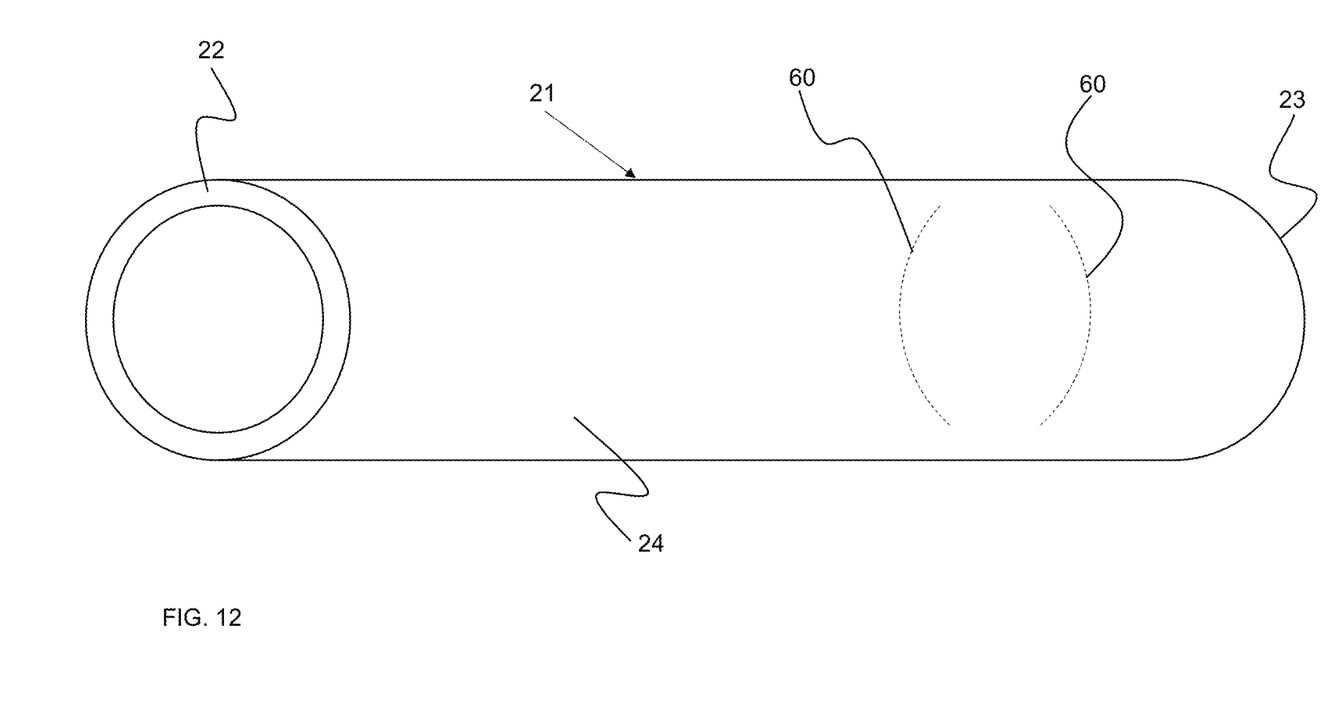
FIG. 12 shows a glass tube portion with filament areas.

FIG. 12 shows a glass tube portion 21 as an example of a glass precursor for producing an ampoule. The glass tube portion has portion ends 22, 23 produced by separation, and has filament areas 60 at predetermined distances from these portion ends 22, 23. By way of example, the filament regions 60 occupy two opposing 120° segments with ends that are spaced by 60° from each other. To produce an ampoule, a glass wall region 24 between portion end 22 and filament areas 60 is expanded in a warm state, and the portion ends 22, 23 are prepared for being sealed, whereafter the ampoule is filled and sealed.

It will be apparent to those skilled in the art that the embodiments as described above are meant by way of example only and that the invention is not limited thereto, but rather can be varied in many ways without thereby departing from the scope of the claims. Furthermore, it will be appreciated that the features, whether disclosed in the specification, the claims, the figures, or otherwise, define essential components of the invention also individually, even if described together with other features.

LIST OF REFERENCE NUMERALS

1 Feeding device
2 Glass tube
20 Separation plane
21 Glass tube portion
22, 23 End of portion
24 Glass wall region
200 Radius vector
3 Irradiation device
30 Focused radiation
31 Focusing optics
32 Laser
33 Guide head
34 Hollow fiber
35 Distance sensor
36 Scanning sensor
300 Irradiation axis
4 Guiding device
41 Scanner head
42 Annular mirror
43 Mirror portion
44 Portion of annular mirror
5 Take-off device
6 Filament
60 Filament area
61 Filament spacing
8 Separation device

What is claimed is:

1. A tubular glass precursor or glass product, comprising a glass tube including filaments, the filaments being provided in a separation plane that is perpendicular a to a longitudinal axis of the glass tube and extending obliquely to local wall radii at an angle that is in a range from 1° to 15°.

2. The tubular glass precursor or glass product of claim 1, wherein the glass precursor or glass product is in a form selected from the group consisting of an ampoule, a cartridge, and a syringe body.

3. The tubular glass precursor or glass product of claim 1, wherein the filaments provide a breaking point along the separation plane for later separation.

4. A glass tube or glass tube precursor, comprising a fracture surface produced at an end of a glass tube the fracture surface comprising broken-open filaments that extend obliquely to local wall radii at an angle that is in a range from 1° to 15°.

5. The glass tube or glass tube precursor of claim 4, wherein the broken-open filaments are arranged with a spacing from each other in a range from 2 µm to 15 µm.

6. The glass tube or glass tube precursor of claim 4, wherein the broken-open filaments belong to two or more filament areas distributed around a circumference of the fracture surface at the end of the glass tube.

7. The glass tube or glass tube precursor of claim 6, further comprising unaffected areas between the two or more filament areas that have an extent of at least 50 µm measured in the circumferential direction at the end of the glass tube, wherein the unaffected areas do not include broken-open filaments.

8. The glass tube or glass tube precursor of claim 6, wherein the two or more filament areas comprise up to twelve areas.

9. The glass tube or glass tube precursor of claim 6, wherein the two or more filament areas occupy at least 8% of the circumference.

10. The glass tube or glass tube precursor of claim 6, further comprising at least one predetermined breaking plane with filaments extending obliquely relative to the local radius.

11. A tubular glass precursor or tubular glass product, comprising a glass tube having a local diameter ranging from 3 mm to 50 mm and an end comprising broken-open filaments, wherein the broken-open filaments belong to two filament areas each occupying a 120° segment around a circumference of the glass tube; and
    wherein the two filament areas are spaced apart by 60° from each other and separated by unaffected areas having no broken-open filaments.

12. The tubular glass precursor or glass product of claim 11, wherein the local diameter ranges from 5 to 40 mm.

13. A tubular glass precursor or tubular glass product comprising a glass tube having a clean fracture surface, comprising broken-open filaments that are free of any chipping or particles greater than 150 μm,
    wherein the broken-open filaments extend obliquely to local wall radii of the glass tube at an angle that is in a range from 1° to 15°.

14. The tubular glass precursor or tubular glass product of claim 13, wherein the clean fracture surface is free of any chipping or particles greater than 100 μm.

15. The tubular glass precursor or tubular glass product of claim 13, wherein the clean fracture surface is free of any chipping or particles greater than 50 μm.

16. The tubular glass precursor or tubular glass product of claim 13, wherein the clean fracture surface is free of any chipping or particles greater than 20 μm.

* * * * *